United States Patent [19]

Munson, Jr.

[11] 4,198,414
[45] Apr. 15, 1980

[54] COMPOUNDS AND METHODS FOR TREATING DIABETIC COMPLICATIONS

[75] Inventor: Harry R. Munson, Jr., Richmond, Va.

[73] Assignee: A. H. Robins Company, Inc., Richmond, Va.

[21] Appl. No.: 865,480

[22] Filed: Dec. 29, 1977

[51] Int. Cl.² ............... A61K 31/40; C07D 209/60
[52] U.S. Cl. .................................. 424/258; 546/94
[58] Field of Search ............... 260/289 C; 424/258; 546/94

[56] References Cited

U.S. PATENT DOCUMENTS

| 3,917,838 | 11/1975 | Bass et al. | 260/289 C |
| 4,015,005 | 3/1977 | Hardtmann | 546/94 |

FOREIGN PATENT DOCUMENTS

| 446341 | 3/1968 | Switzerland | 260/289 C |

OTHER PUBLICATIONS

Dvornik et al., "Science", 182, pp. 1146 & 1147 (1973).

*Primary Examiner*—Glennon H. Hollrah
*Assistant Examiner*—D. B. Springer

[57] ABSTRACT

Novel 4-H-pyrrolo[3,2,1-ij]quinolin-1,2-diones having the formula

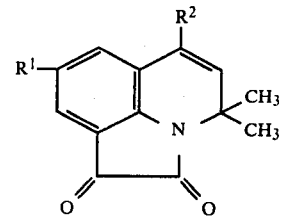

wherein $R^1$ is hydrogen or methyl and $R^2$ is methyl or phenyl are disclosed. The compounds are useful as inhibitors of aldose reductase.

12 Claims, No Drawings

COMPOUNDS AND METHODS FOR TREATING DIABETIC COMPLICATIONS

BACKGROUND OF THE INVENTION

1. Field of the Invention

The present invention is concerned with certain novel 4-H-pyrrolo[3,2,1-ij]quinolin-1,2-diones and methods for their preparation. The invention is also concerned with the use of the novel compounds as inhibitors of aldose reductase and for the prevention and treatment of various diabetic complications including cataracts, neuropathy, retinopathy and nephropathy.

2. Description of the Prior Art

It has been established that high levels of polyols such as sorbitol and galactitol accumulate in certain tissues of the human body as, for example, in galactosemia and certain diabetic complications. The polyols are formed in the body by the enzymatic reduction of various hexoses such as glucose and galactose by the enzyme aldose reductase. In particular, the accumulation of the polyols in the lens and retina tissue of diabetic persons is responsible for the formation of cataracts and the concomitant loss of lens clarity. The investigations of Kenneth H. Gabby, New England Journal of Medicine 288 (16), 831–836 (1973) and references cited therein, and J. H. Kinoshita et al, Biochem. Biophys. Acta., 158, 472 (1968) and references cited therein have shown that inhibitors of aldose reductase effectively delay cataract formation in rats fed galactose. Thus, an agent which inhibits aldose reductase affords a potential means of preventing cataract formation in persons afflicted with diabetes and galactosemia. U.S. Pat. No. 3,821,383 discloses certain benzoquinoline acetic acids as useful in preventing or relieving diabetic complications. Science, 182 1146 (1973) discloses 1,3-dioxo-1H-benz[de]isoquinoline-2(3H) acetic acid (AY-22,284) as an aldose reductase inhibitor which effectively suppressed the formation of cataracts in galactosemic rats.

SUMMARY OF THE INVENTION

According to the present invention there are provided certain novel 4H-pyrrolo[3,2,1-ij]quinoline-1,2-diones of the formula:

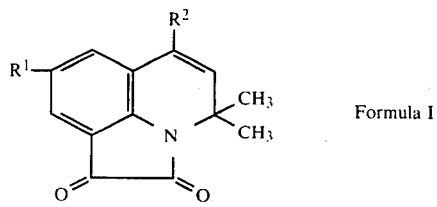

Formula I wherein;
R$^1$ is hydrogen or methyl, and
R$^2$ is methyl or phenyl,
pharmaceutical compositions containing the compounds as active ingredients and methods for the use of said pharmaceutical compositions in diabetic mammals for the prophylaxis and treatment of diabetic complications.

The preparation of 4-H-pyrrolo[3,2,1-ij]quinoline-1,2-diones (I) may be accomplished by mixing and reacting the appropriately substituted 1,2-dihydroquinoline (II) with oxalyl chloride (III). The reaction sequence is illustrated by the following:

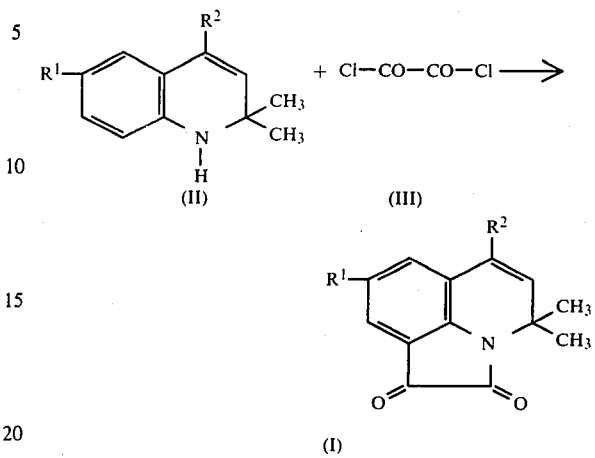

wherein R$^1$ and R$^2$ are as defined hereinabove.

Generally speaking, the reaction of a 1,2-dihydroquinoline (II) with oxalyl chloride (III) to give a 4-H-pyrrolo[3,2,1-ij]quinolin-1,2-dione (I) is carried out in a dry aprotic solvent by the dropwise addition of a solution of the 1,2-dihydroquinoline in the same solvent to the stirred solution of oxalyl chloride in an inert atmosphere at or near room temperature. Subsequent to the addition the reaction mixture is briefly stirred at ambient temperature and then at gentle reflux to complete the reaction. The solvent is stripped from the reaction mixture at reduced pressure to give a solid residue which on crystallization from a selected solvent or solvent system furnishes the 4-pyrrolo[3,2,1-ij]quinoline-1,2-dione I.

It is therefore an object of the present invention to provide novel 4H-pyrrolo[3,2,1-ij]quinoline-1,2-diones and methods for their preparation. Another object is to provide compositions containing the novel 4H-pyrrolo[3,2,1-ij]quinoline-1,2-diones and a pharmaceutical carrier. A still further object is to provide a method for the use of compositions containing the novel 4H-pyrrolo[3,2,1-ij]quinoline-1,2-diones for the prophylaxis and treatment of diabetic complications. These and other objects will become apparent from the description which follows.

DETAILS OF THE INVENTION

As disclosed hereinabove, sugar cataract formation is a frequent complication of the diabetic patient and their occurrence is apparent even in patients where diabetes appears controlled. The involvement of the enzyme aldose reductase in the formation of sugar cataracts has been demonstrated as shown in the discussion of the prior art, said aldose reductase catalyzing the production of sorbitol from glucose and glactitol (dulcitol) from galactose. The accumulation of polyols in the lens tissue results in osmotic and histological changes which are characteristic of sugar cataracts. More specifically, galactose has been shown to be a cataractogenic agent and the inhibition of cataract formation in galactose fed rats provides a means for evaluating the efficacy of a chemical entity for the prophylaxis and treatment of polyol induced cataracts.

Male albino rats of the Sprague-Dawley strain weighing 300–450 g. were used to evaluate the efficacy of certain drugs as aldose reductase inhibitors. Control rats received a 10% galactose solution at a dose level of 10 ml/kg. daily for three days. The total dose was 1 g/kg. daily. Six animals per control group were used. Groups receiving galactose plus test drug contained three rats. The routine starting dose of a test drug was 100 mg/kg. orally daily for three days with galactose given simultaneously. The test drug was administered at a volume of 5 ml/kg. The test drug solution and the galactose solution were administered together. Twenty-four hours after the third dose the lens of the eyeballs were carefully removed from the sacrificed rats and the polyol content of the lens determined according to West and Rapport, Proc. Soc. Exp. Biol. Med. 70, 141–142 (1949).

The compounds of Examples 1-3 were tested according to the foregoing procedure at a dose level of 100 mg/kg. orally. When compared to the control animals, the compounds of Examples 1-3 exhibited a 29%, 25% and a 21% reduction in mean polyol accumulation respectively.

The following preparations and examples are given by way of illustration only and are not to be construed as limiting.

PREPARATION 1

1,2-Dihydro-2,2,4,6-tetramethylquinoline Hydrochloride

To a stirred hot melt of p-toluidine (160.5 g., 1.5 mole) and iodine (4.5 g., 0.0177 mole) jacketed by an oil bath (185° C.) was added dropwise acetone (335 g., 5.77 moles) so that each drop entered the melt just below the surface. The rate of addition was adjusted so that about one drop/second of water-acetone was distilled from the reaction. A melt temperature of approximately 175° C. was maintained during the 3-hour addition period. A 335 ml. volume of distillate was collected. The dark reaction mixture was fractionated by vacuum distillation. The fraction b.p. 108°–150° C./25 mm., (58 g.) was collected and reserved. The fraction b.p. 88°–103° C./0.1 mm. contained the desired product. The fraction b.p. 108°–150° C./25 mm. was freed of unreacted toluidine by dissolving in ligroine, chilling and filtering off the crystalline toluidine. The filtrate was added to fraction b.p. 88°–103° C./0.1 mm. and the mixture distilled yielding ca. 150 g. (53% yield) shown by conventional methods to be pure product. A portion of the distilled base (42.11 g., 0.226 mole) was converted to the hydrochloride salt. The hydrochloride salt after several recrystallizations from anhydrous ethanol melted at 120°–122.5° C.

Analysis: Calculated for $C_{13}H_{18}ClN$: C,69.79; H,8.11; N,6.26; Found: C,69.95; H,8.11; n,6.21.

PREPARATION 2

1,2-Dihydro-2,2-dimethyl-4-phenylquinoline

Calcium chloride dihydrate (11 g., 0.075 m), cuprous chloride (6.6 g., 0.073 m), and 0.5 g. copper dust were added to 70 ml. concentrated hydrochloric acid and chilled to −5° C. The slurry was treated with 2-hydroxy-2-methyl-4-phenyl-3-butyne (24 g., 0.15 m) by portionwise addition with stirring over a 45-minute period. When addition was complete, the mixture was stirred 1 hr. at 0° C., then allowed to warm to ambient temperature over a 60 minute period. The solid was removed by vacuum filtration; the oily layer in the filtrate was separated and washed twice with 15 ml. cold concentrated hydrochloric acid. The aqueous acid was extracted twice with small volumes of petroleum ether, and these extracts added to the previously separated oily layer. The organic liquid was dried over two changes of magnesium sulfate. Volatile material was removed at <50° C./30 mm. and the residual syrup added dropwise with stirring to a solution/suspension of aniline (16.8 g., 0.18 m), triethylamine (20.2 g., 0.2 m), and 0.1 g. each of copper dust and cuprous chloride in 200 ml. ether. The resultant mixture was stirred at ambient temperature for 18 hrs. The reaction mixture was then filtered using Celite to remove fine particulate matter. The filtrate was washed carefully with 5% sodium carbonate solution and the ether separated, dried, and concentrated. Fractionation of the residue yielded a fraction b.p. 156°–160° C./0.3 mm., 17.5 g. which was redistilled to yield 13.6 g, b.p. 116°–120° C./0.1 mm. A portion was recrystallized from 60°–110° C. ligroine and from isopropanol 70%, to furnish an off-white crystalline solid melting at 79.5°–81° C.

Analysis: Calculated for $C_{17}H_{17}N_1O$: C,86.76; H,7.28; N,5.95; Found: C,86.51; H,7.32; N,5.84.

PREPARATION 3

1,2-Dihydro-2,2,4-trimethylquinoline Hydrochloride 1,2-Dihydro-2,2,4-trimethylquinoline was prepared according to the procedures of Preparation 1 and the hydrochloride salt prepared from the free base melted at 211°–216.5° C.

Analysis: Calculated for $C_{12}H_{16}ClN$: C,68.73; H,7.69; N,6.68; Found: C,68.58; H,7.73; N,6.73.

EXAMPLE 1

4,4,6,8-Tetramethyl-4H-pyrrolo[3,2,1-ij]quinolin-1,2-dione 1,2-Dihydro-2,2,4,6-tetramethylquinoline (16.7 g., 0.09 mole) in 50 ml. dry methylene chloride was added slowly dropwise with stirring to oxalyl chloride (12.6 g., 0.1 mole) in 150 ml. dry methyl chloride under nitrogen at 30° C. Addition required 20 min., and when complete the very dark solution was stirred 15 min. at ambient temperature and one hour at a gentle reflux. The solvent was removed at reduced pressure and the dark red residue crystallized from methanol to yield a solid melting at 157°–161° C. Two additional recrystallizations from 25% chloroform in ligroine (60°–110° C.) gave a deep red crystalline solid melting at 163.5°–165.5° C. The yield was 44%.

Analysis: Calculated for $C_{15}H_{15}NO_2$: C,74.66; H,6.26; N,5.80; Found: C,74.55; H,6.27; N,5.75.

EXAMPLE 2

4,4,6-Trimethyl-4H-pyrrolo[3,2,1-ij]quinolin-1,2-dione

A solution of 1,2-dihydro-2,2,4-trimethylquinoline (34.6 g., 0.2 mole) in 50 ml. dry methylene chloride was added slowly dropwise to oxalyl chloride (26.4 g., 0.21 mole) in 300 ml. dry methylene chloride. Addition required 45 min., and when complete the resultant solution was stirred at ambient temperature 4 hrs. and refluxed 2 hrs. The dark red solution was freed of solvent at reduced pressure and the very dark solid residue taken up in chloroform. Dilution with ligroine and chilling produced a total yield of 32.6 g. (71.8%); m.p. 170°–176° C. A sample repeatedly recrystallized from toluene-ligroine (1:4) melted at 176°–177.5° C.

Analysis: Calculated for $C_{14}H_{13}NO_2$: C,73.99; H,5.76; N,6.16; Found: C,73.89; H,5.78; N,5.99.

EXAMPLE 3

4,4-Dimethyl-6-phenyl-4H-pyrrolo[3,2,1-ij]quinolin-1,2-dione

A solution of 1,2-dihydro-2,2-dimethyl-4-phenyl-quinoline (5.0 g., 21.2 mMole) in 50 ml. dry methylene chloride was added dropwise with stirring to oxalyl chloride (2.77 g., 22.0 mMole) in 200 ml. dry methylene chloride at 30° C. and protected from moisture. Addition required one hour, and when complete the orange solution was stirred 30 minutes at ambient temperature and two hours at reflux. The solvent was removed at reduced pressure and the purple-brown crystalline residue air dried. A single recrystallization from chloroform/60°–110° C. ligroine produced a solid 3.97 g. (63.5%) melting at 210.5°–212° C.

Analysis: Calculated for $C_{19}H_{15}N_1O_2$: C,78.87; h,5.23; N,4.84; Found: C,78.53; H,5.23; N,4.78.

Formulation and Administration

The invention further provides pharmaceutical compositions comprising, as active ingredient, the novel compounds according to the invention in association with a pharmaceutical carrier or excipient. The compounds may be presented in a form suitable for oral or parenteral administration. Thus, for example, compositions for oral administration are solid or liquid and can take the form of capsules, tablets, coated tablets, suspensions, etc., employing such carriers or excipients conveniently used in the pharmaceutical art. Suitable tableting excipients include lactose, potato and maize starches, talc, gelatin and steric and silicic acids, magnesium stearate and polyvinyl pyrrolidone.

For parenteral administration, the carrier or excipient can be a sterile, parenterally acceptable liquid, e.g., water, or a parenterally acceptable oil, e.g., arachis oil, contained in ampoules.

Advantageously, the compositions are formulated as dosage units, each unit being adapted to supply a fixed effective dose of active ingredient. Unit dosages are usually from 5 milligrams or above and preferably 25, 50 or 100 milligrams. Obviously, several unit dosage forms may be administered at about the same time.

The following are examples formed in accordance with this invention:

(1) Capsules

Capsules of 5 mg., 25 mg., 50.0 mg. and 100.0 mg. of active ingredient per capsule are prepared.

| Typical blend of encapsulation | mg. per capsule |
|---|---|
| Active ingredient | 5.0 |
| Lactose | 140.0 |
| Starch | 40.0 |
| Total | 185.0 |

Uniformly blend the active ingredient with lactose and starch and encapsulate the blend.

Additional capsule formulations contain a higher dose of active ingredient and are as follows:

| Ingredients | 25 mg. per Capsule | 50 mg. per Capsule | 100 mg. per Capsule |
|---|---|---|---|
| Active ingredient | 25.0 | 50.0 | 100.0 |
| Lactose | 300.0 | 271.7 | 231.5 |
| Starch | 110.0 | 113.0 | 103.5 |
| Total | 435.0 | 435.0 | 435.0 |

(2) Tablets

A typical formulation for a tablet containing 5.0 mg. of active ingredient per tablet follows. The formulation may be used for other strengths of active ingredient by adjustment of weight of dicalcium phosphate.

|  | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
| Total | 170.1 |

Uniformly blend 1, 2, 4 and 5. Prepare 3 as 10 percent paste in water. Granulate the blend with starch paste and press the wet mass through an eight mesh screen. The wet grnaulation is dried and sized through a twelve mesh screen. The dried granules are blended with the calcium stearate and compressed.

Additional tablet formulations contain 25.0 mg., 50.0 mg. and 100.0 mg. of active ingredient per tablet. The tablets are prepared according to the foregoing formulation by adjustment of weight of dicalcium phosphate.

INTRAMUSCULAR INJECTION

Ingredients:
1. Active ingredient—mg. 5.0
2. Isotonic buffer solution 4.0, q.s. to ml. 2.0

Procedure:
(1) Dissolve the active ingredient in the buffer solution.
(2) Aseptically filter the solution from No. 1.
(3) The sterile solution is now aseptically filled into sterile ampoules.
(4) The ampoules are sealed under aseptic conditions.

Various modifications and equivalents will be apparent to one skilled in the art and may be made in compositions, methods and procedures of the present invention without departing from the spirit or scope thereof, and it is therefore to be understood that the invention is to be limited only by the scope of the appended claims.

I claim:

1. A compound selected from 4H-pyrrolo[3,2,1-ij]quinoline-1,2-diones having the formula:

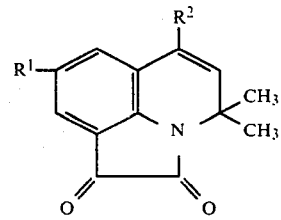

wherein;
$R^1$ is hydrogen or methyl, and
$R^2$ is methyl or phenyl.

2. The compound of claim 1 which is 4,4,6,8-tetramethyl-4H-pyrrolo[3,2,1-ij]quinolin-1,2-dione.

3. The compound of claim 1 which is 4,4,6-trimethyl-4H-pyrrolo[3,2,1-ij]quinolin-1,2-dione.

4. The compound of claim 1 which is 4,4-dimethyl-6-phenyl-4H-pyrrolo[3,2,1-ij]quinolin-1,2-dione.

5. A method for reducing polyol accumulation in the lens tissue of a mammal which consists essentially of administering to said mammal an amount of a compound having the formula:

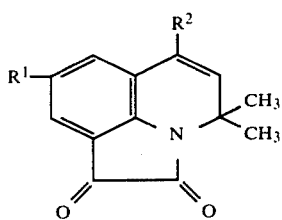

wherein;
$R^1$ is hydrogen or methyl, and
$R^2$ is methyl or phenyl
effective in bringing about said reduced polyol accumulation.

6. The method of claim 5 wherein the compound is 4,4,6,8-tetramethyl-4H-pyrrolo[3,2,1-ij]quinolin-1,2-dione.

7. The method of claim 5 wherein the compound is 4,4,6-trimethyl-4H-pyrrolo[3,2,1-ij]quinolin-1,2-dione.

8. The method of claim 5 wherein the compound is 4,4-dimethyl-6-phenyl-4H-pyrrolo[3,2,1-ij]quinolin-1,2-dione.

9. A pharmaceutical composition for reducing polyol accumulation in the lens tissue of mammals comprising (a) an amount of a compound having the formula:

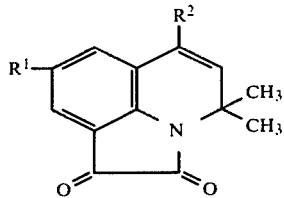

wherein;
$R^1$ is hydrogen or methyl, and
$R^2$ is methyl or phenyl effective in reducing said polyol accumulation, and
(b) a pharmaceutically acceptable carrier.

10. The composition of claim 9 wherein the compound is 4,4,6,8-tetramethyl-4H-pyrrolo[3,2,1-ij]quinolin-1,2-dione.

11. The composition of claim 9 wherein the compound is 4,4,6-trimethyl-4H-pyrrolo[3,2,1-ij]quinolin-1,2-dione.

12. The composition of claim 9 wherein the compound is 4,4-dimethyl-6-phenyl-4H-pyrrolo[3,2,1-ij]quinolin-1,2-dione.

* * * * *